(12) United States Patent
Kirsch et al.

(10) Patent No.: US 10,868,257 B2
(45) Date of Patent: Dec. 15, 2020

(54) DITHIOALKYLPYRROLOPYRROLES AND THE USE THEREOF AS DYES

(71) Applicant: Merck Patent GmbH, Darmstadt (DE)

(72) Inventors: Peer Kirsch, Seeheim-Jugenheim (DE); Susann Beck, Darmstadt (DE); Michael Junge, Pfungstadt (DE); Ursula Patwal, Reinheim (DE); Mila Fischer, Muehltal (DE)

(73) Assignee: Merck Patent GmbH, Darmstadt (DE)

( * ) Notice: Subject to any disclaimer, the term of this patent is extended or adjusted under 35 U.S.C. 154(b) by 93 days.

(21) Appl. No.: 15/742,918

(22) PCT Filed: Jun. 20, 2016

(86) PCT No.: PCT/EP2016/001048
§ 371 (c)(1),
(2) Date: Jan. 9, 2018

(87) PCT Pub. No.: WO2017/008880
PCT Pub. Date: Jan. 19, 2017

(65) Prior Publication Data
US 2018/0375030 A1    Dec. 27, 2018

(30) Foreign Application Priority Data

Jul. 10, 2015  (EP) .................................. 15002069

(51) Int. Cl.
| | |
|---|---|
| *G02F 1/1333* | (2006.01) |
| *H01L 51/00* | (2006.01) |
| *C07D 487/04* | (2006.01) |
| *G02B 5/22* | (2006.01) |
| *C09K 19/34* | (2006.01) |
| *C09K 19/60* | (2006.01) |
| *C07D 487/22* | (2006.01) |
| *H01L 51/50* | (2006.01) |

(52) U.S. Cl.
CPC ........ *H01L 51/0072* (2013.01); *C07D 487/04* (2013.01); *C07D 487/22* (2013.01); *C09K 19/3477* (2013.01); *C09K 19/3488* (2013.01); *C09K 19/60* (2013.01); *G02B 5/223* (2013.01); *H01L 51/0068* (2013.01); *H01L 51/504* (2013.01)

(58) Field of Classification Search
CPC ............ C09K 19/3477; C09K 19/3488; C09K 19/60; G02F 1/1333; G02B 5/223; C07D 487/04; C07D 487/22
USPC ...................................... 252/299.61
See application file for complete search history.

(56) References Cited

U.S. PATENT DOCUMENTS

| | | | |
|---|---|---|---|
| 10,202,508 B2 | 2/2019 | Tong et al. | |
| 2018/0375030 A1* | 12/2018 | Kirsch | ................. C07D 487/04 |

FOREIGN PATENT DOCUMENTS

WO     2015090497 A1    6/2015

OTHER PUBLICATIONS

"Near-Infrared Thermochromic Diazapentalene Dyes and Polymers", Advanced Material (Weinheim, Germany) vol. 24, Issue 1, pp. 1582-1588.*
"Near-Infrared Thermochromic Diazapentalene Dyes and Polymers", Advanced Material (Weinheim, Germany), 2012, vol. 24, Issue 1, pp. 1582-1588 (Year: 2012).*
International Search Report PCT/EP2016/001048 dated Aug. 29, 2016.
Gang Qian et al: "Synthesis and study of low-bandgap polymers containing the diazapentalene and diketopyrrolopyrrole chromophores for potential use in solar cells and near-infrared photodetectors", Journal of Materials Chemistry, vol. 22, No. 25, Jan. 1, 2012 (Jan. 1, 2012), GB, pp. 12867, XP055295265, ISSN: 0959-9428.
Gang Qian et al: "Family of Diazapentalene Chromophores and Narrow-Band-Gap Polymers: Synthesis, Halochromism, Halofluorism, and Visible-Near Infrared Photodetectivity", Chemistry of Materials, vol. 24, No. 12, Jun. 26, 2012 (Jun. 26, 2012), US, pp. 2364-2372, XP055295267, ISSN: 0897-4756.
Gang Qian et al: "Near-Infrared Thermochromic Diazapentalene Dyes", Advanced Materials, vol. 24, No. 12, Feb. 20, 2012 (Feb. 20, 2012), DE, pp. 1582-1588, XP055295270, ISSN: 0935-9648.
Notice for Reasons for Rejection in corresponding JP application 2018-500740 dated May 20, 2020 (English—pp. 1-4).

* cited by examiner

*Primary Examiner* — Geraldina Visconti
(74) *Attorney, Agent, or Firm* — Millen White Zelano and Branigan, PC; Csaba Henter

(57) ABSTRACT

Novel dithiopyrrolopyrrole derivatives having dichroic properties which have very high photostability in solution in a liquid-crystalline host are proposed.

23 Claims, No Drawings

DITHIOALKYLPYRROLOPYRROLES AND THE USE THEREOF AS DYES

FIELD OF THE INVENTION

The invention is in the field of organic dye chemistry and relates to novel dichroic dyes based on dithioalkylpyrrolopyrroles, to a process for the preparation thereof, and to the use thereof.

PRIOR ART

In the field of devices for regulating the entry of light into a room, there is interest in technical solutions by means of which durable and high-performance devices can be obtained.

An advantageous approach for these devices is the use of switching layers comprising a mixture of at least one liquid-crystalline compound in combination with at least one dichroic dye. By application of a voltage, a change in the spatial alignment of the dye molecules can be achieved in these switching layers, effecting a change in their absorption and thus the transmission through the switching layer. A corresponding device is described, for example, in WO 2009/141295.

So-called rylene dyes, specifically perylene and terrylene derivatives, have already been described for use in the said devices, for example in WO 2009 141295 A1 and WO 2013 004677 A1 (UNIV EINDHOVEN), but their stability does not meet the extreme demands for use in windows.

Benzothiadiazole and diketopyrrolopyrrole derivatives are also known as building blocks for such dyes. However, these compounds are more suitable for covering the red and yellow colour space. Blue and green dyes having adequate photostability and strong dichroism are generally based on rylene structures, which are problematic with respect to their solubility in liquid-crystal mixtures.

In this connection, reference is made to the following publications from the prior art: Compounds having a diketopyrrolopyrrole skeleton have already been known for some time. EP 0094911 A1 (CIBA) describes how diketopyrrolopyrrole compounds which contain aryl groups as substituents can be prepared efficiently.

Furthermore, the use of this class of compounds as fluorescent markers and as constituents of organic semiconductors and corresponding semiconductor devices is known (WO 2004 090046 A1, BASF).

The paper by G. Qian and Z. Wang with the title "Near-IR thermochromic diazapentalene dyes", published in Adv. Mater. 24, pp. 1582-1588 (2012), discloses thermochromic dyes which come into consideration, for example for a very wide variety of uses, from paints and textiles to light filters and biosensors. The substances are prepared starting from dithiophenepyrrolopyrrolediones, which are treated firstly with Lawes son's reagent and then with a brominating agent. The dithiopyrrolopyrroledithiones obtained can then be derivatised using a boric acid derivative in the presence of a palladium complex. The reaction is explained in Scheme A below:

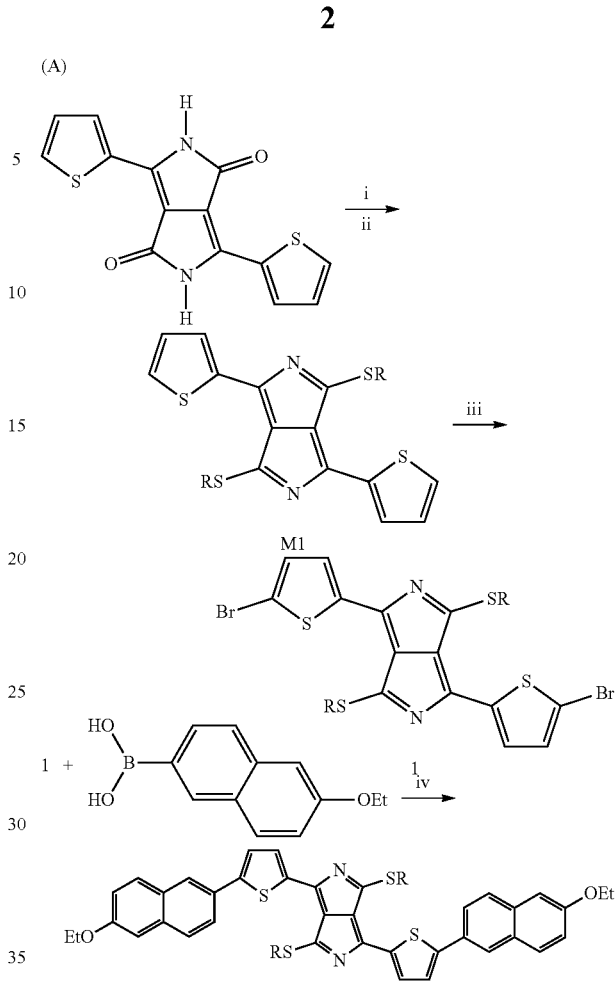

The only substance disclosed specifically here is substance M2, in the case of which the derivatisation is carried out by introduction of an ethoxy-substituted naphthyl radical. The same substances are also described by the same authors in Chem. Mater. 24, pp. 2364-2372 (2012).

The same authors likewise describe dithiopyrrolopyrrole derivatives, which follow Scheme B below:

-continued
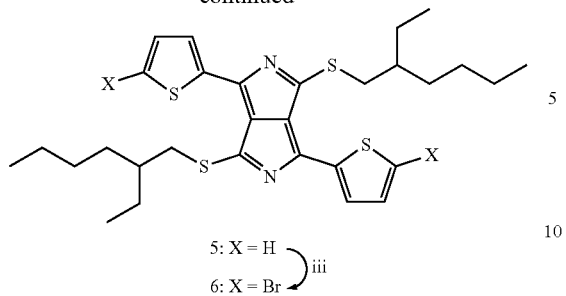
5: X = H  
6: X = Br  } iii
The structures denoted by (5) and (6) serve as intermediates for the preparation of polymeric chromophores, as indicated in Scheme C below:
(C)
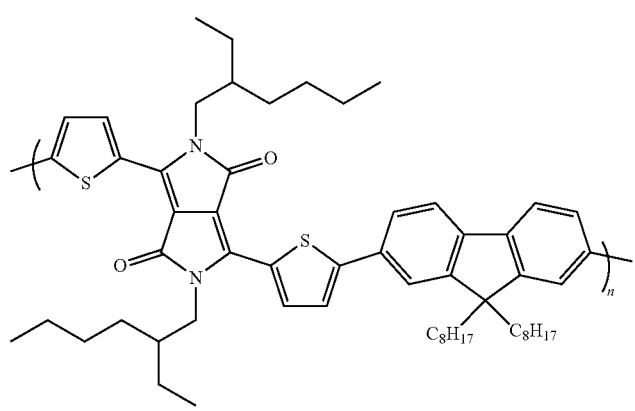
P1
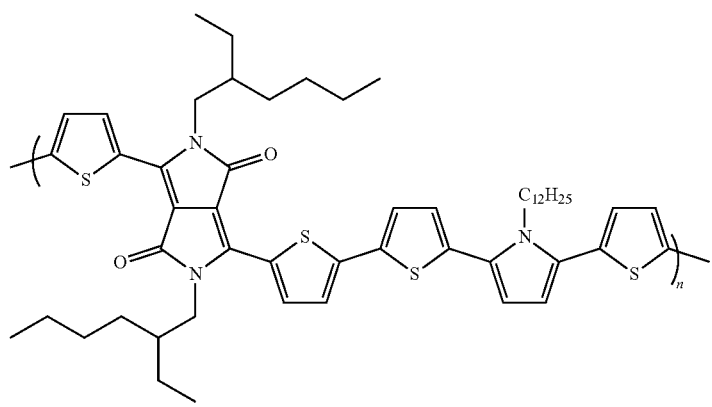
P2
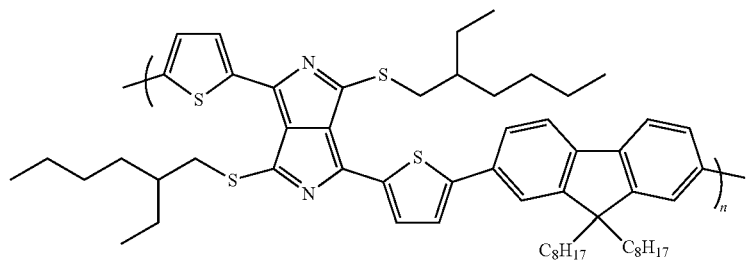
P3

-continued

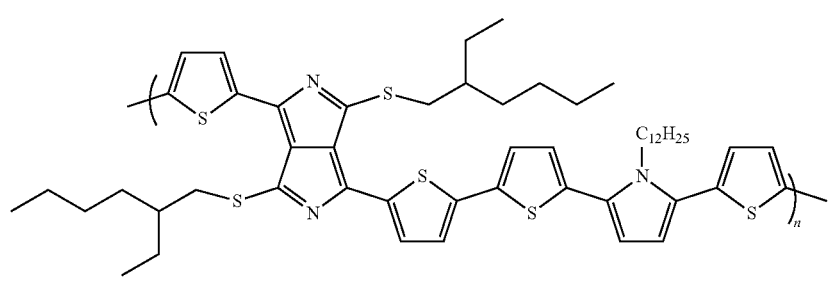

P4

There is a continuous need for improvement regarding dichroic dyes for use in devices for regulating the entry of light into rooms, in particular with respect to light stability, long-term stability of the solution and high degree of anisotropy of the absorption.

The object of the present invention was therefore to provide novel dyes having dichroic properties which are superior to the prior-art substances and are distinguished, in particular, by improved photostability and high solubility.

DESCRIPTION OF THE INVENTION

The invention relates firstly to dithiopyrrolopyrrole derivatives of the formula (1)

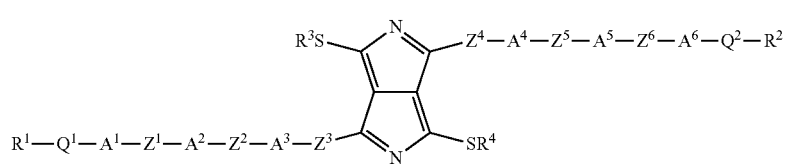

1 in which
$R^1$, $R^2$, $R^3$ and $R^4$, independently of one another, stand for linear or branched, optionally halogen-substituted alkyl groups having 1 to 20 carbon atoms or halogen;
$Q^1$ and $Q^2$ each denote single bonds or stand, independently of one another, for O, $OCF_2$, $CF_2$, $CF_2CF_2$ or CO;
$A^1$, $A^2$, $A^3$, $A^4$, $A^5$ and $A^6$ each denote single bonds or stand, independently of one another, for a group formed by phenylene, pyridine, pyrimidine, pyridazine, naphthylene, thiophene, selenophene and thiazole, with the proviso that
(i) at least $A^3$ and $A^4$ represent aromatic ring structures and
(ii) the aromatic ring structures are optionally substituted by halide; and
$Z^1$, $Z^2$, $Z^3$, $Z^4$, $Z^5$ and $Z^6$ each denote single bonds or stand, independently of one another, for a radical selected from the group formed by C≡C, CH=CH, CF=CF, CF=CH, $CH_2CH_2$, $CF_2$—$CF_2$ and $CF_2O$, with the proviso that
(iii) at least $Z^3$ and $Z^4$ represent either single bonds or a π-conjugated group.

Surprisingly, it has been found that the substances of the formula (1) satisfy the requirement profile in its entirety. In particular, the substances in solution in a liquid-crystalline host exhibit extreme photostability, which is clearly superior, in particular, to that of rylene derivatives in general and perylenediimide derivatives in particular. At the same time, they exhibit high dichroism and very good solubility.

For the purposes of the present invention, an alkyl group having 1 to 20 C atoms is preferably taken to mean the radicals methyl, ethyl, n-propyl, i-propyl, n-butyl, i-butyl, s-butyl, t-butyl, 2-methylbutyl, n-pentyl, s-pentyl, cyclopentyl, neopentyl, n-hexyl, cyclohexyl, neohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl or octynyl.

With respect to their capability, preference is given for the purposes of the invention to derivatives of the formula (1) in which
(i) $R^1$, $R^2$, $R^3$ and $R^4$ stand, independently of one another, for branched alkyl radicals having 6 to 12 carbon atoms; and/or
(ii) 3, 4 or 5 aromatic ring structures are present; and/or
(iii) the aromatic ring structures are substituted by fluoride.

Particular preference is given to structures which have mesophases at temperatures below about 200° C. These substances include, in particular, the following compounds 2, 3, 4, 5, 6 and 7:

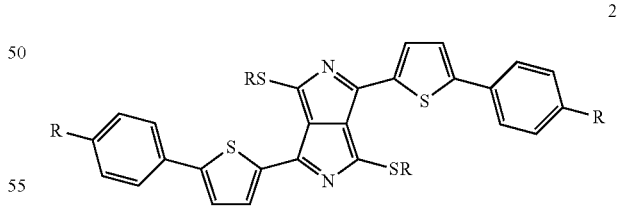

2

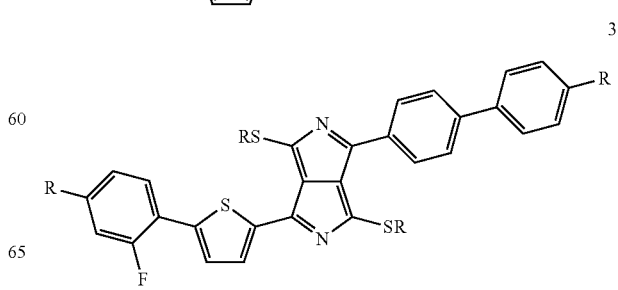

3

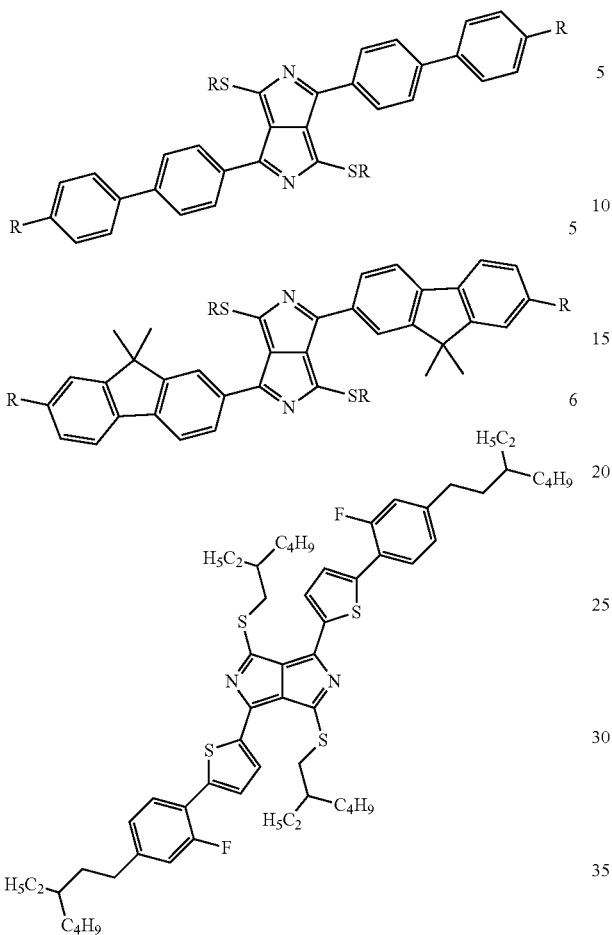
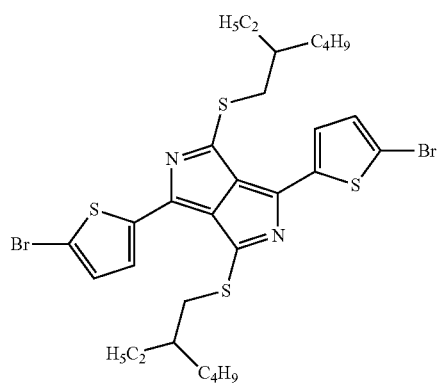
with the proviso that the radicals R have the meaning indicated above.
Preparation Process
The preparation of the dithiopyrrolopyrrole derivatives can generally be described by Scheme D below:

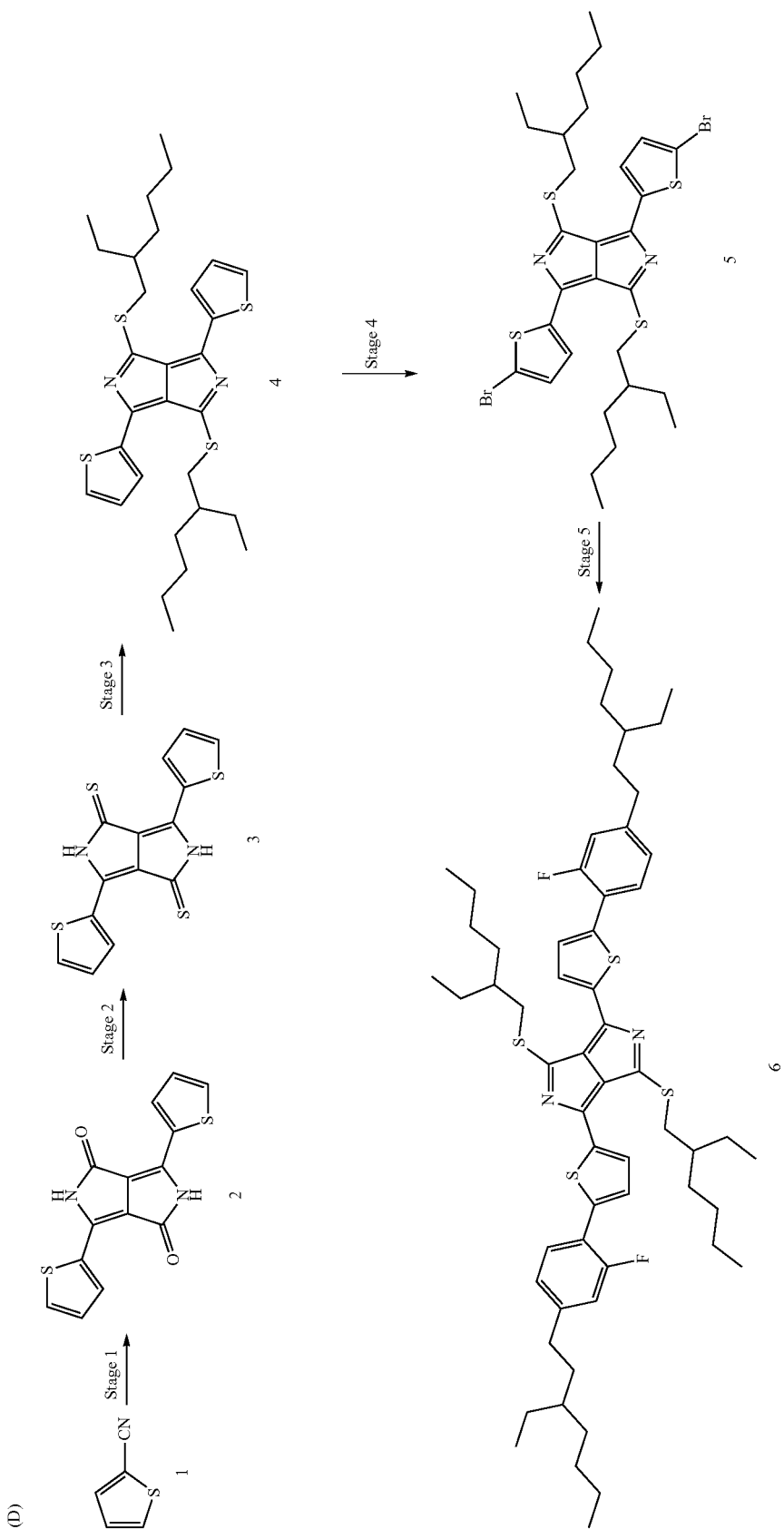

The synthesis sequence is known in principle from the prior art. Reference is made to the article by F. Closs and R. Gompper with the title "2,5-*Diazapentalen*" [2,5-Diazapentalene] in Angew. Chem. 99(6), pp. 564-567 (1987) and the papers by G. Quian et al. which were cited in the introduction. The reaction steps are explained in greater detail below for a specific example:

The first step of the synthesis sequence can be carried out by reaction of 2-thiophenecarbonitrile with dimethyl succinate in the presence of sodium hydride and tert-amyl alcohol as solvent.

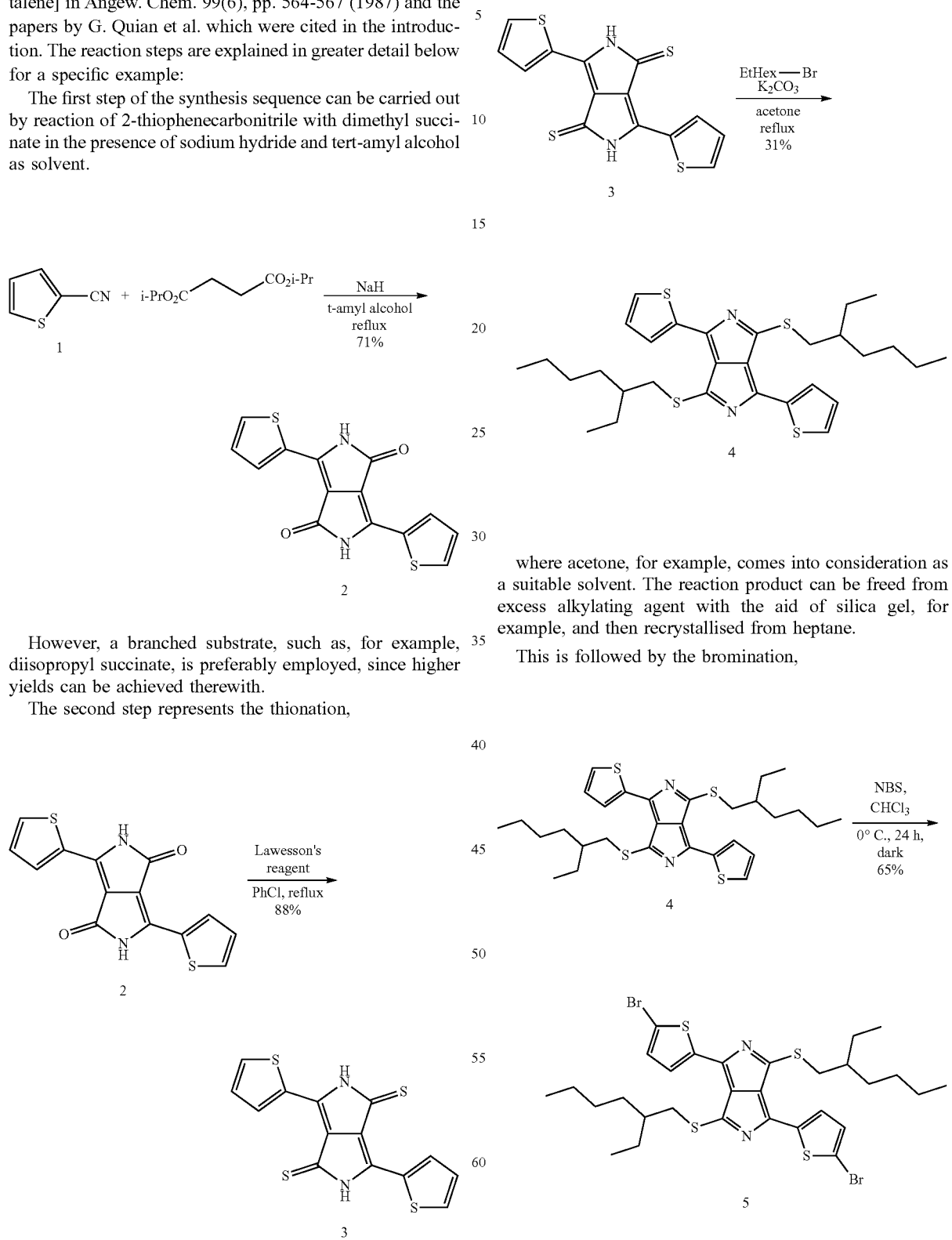

However, a branched substrate, such as, for example, diisopropyl succinate, is preferably employed, since higher yields can be achieved therewith.

The second step represents the thionation, for which Lawesson's reagent, which is known from the prior art, is employed.

For the S-alkylation, which represents the third step, a corresponding alkyl bromide is employed, where acetone, for example, comes into consideration as a suitable solvent. The reaction product can be freed from excess alkylating agent with the aid of silica gel, for example, and then recrystallised from heptane.

This is followed by the bromination, which is carried out, for example, by reaction with N-bromosuccinimide. The final process step is a Suzuki coupling,

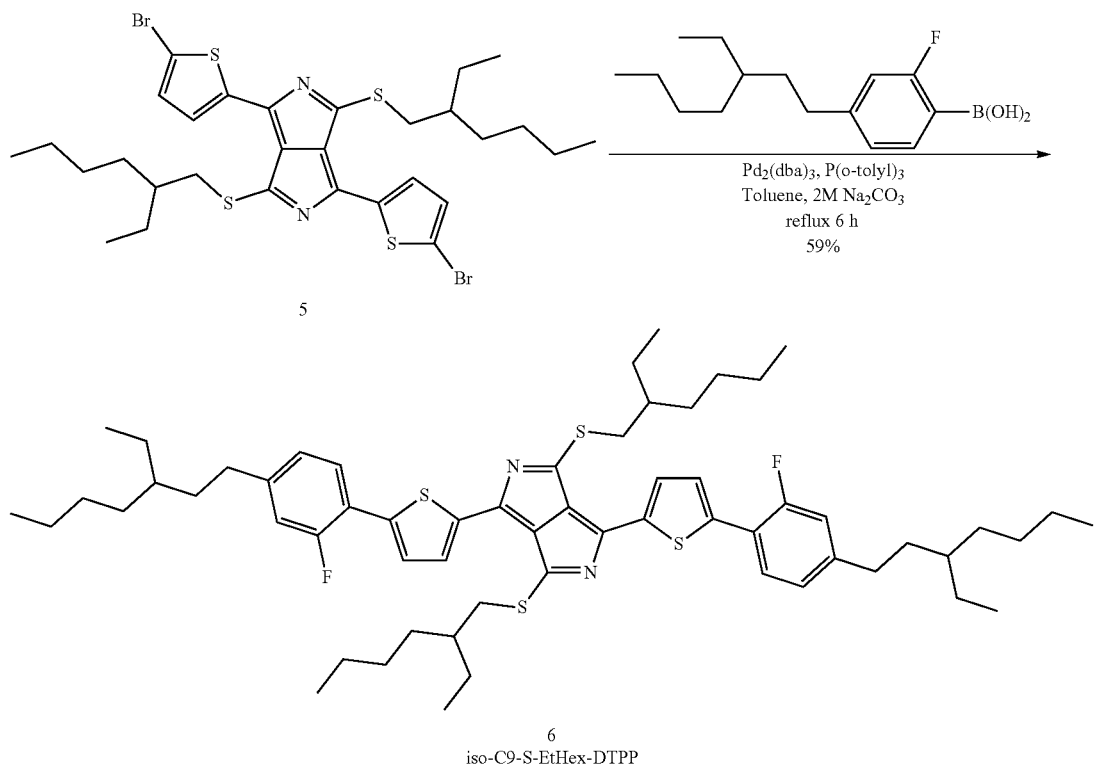

in which the group which replaces the bromide is introduced via a boric acid compound. Suitable catalysts are transition-metal complexes, preferably based on palladium or platinum, which contain phosphines or phosphites as ligands.

For a specific example, the final step can also be described by Scheme E:

(E)

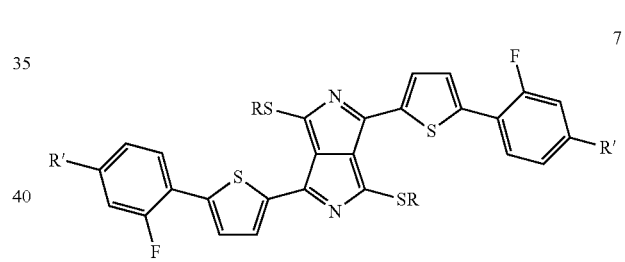

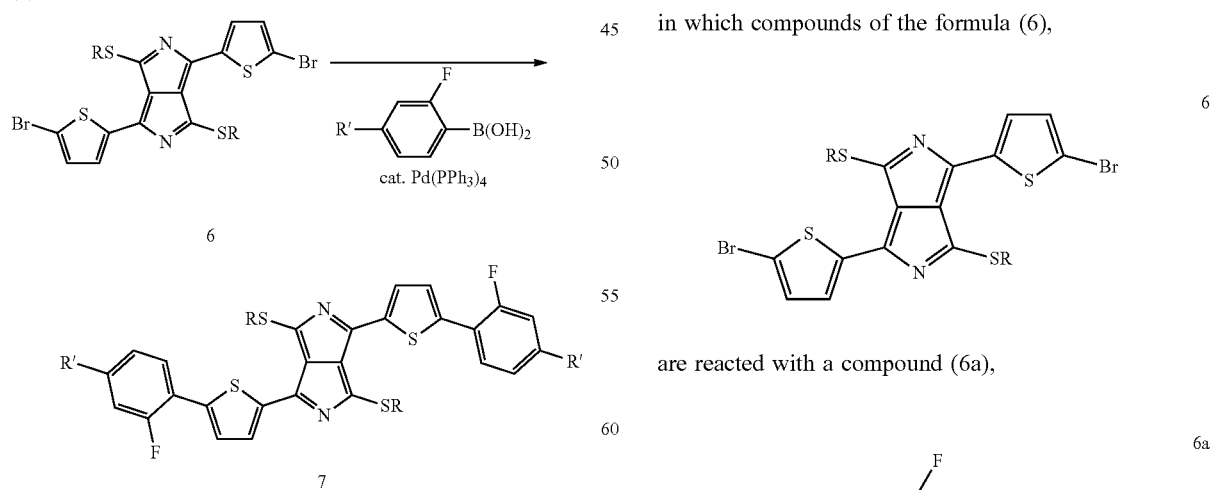

in which compounds of the formula (6), are reacted with a compound (6a),

Correspondingly, the invention furthermore relates to a process for the preparation of the dithiopyrrolopyrrole derivatives of the formula (7), in which R and R' stand, independently of one another, for linear or branched, optionally halogen-substituted alkyl groups having 1 to 20 carbon atoms or halogen, in the presence of a catalytic amount of a homogeneous transition-metal complex. Preferably, both groups denote branched alkyl groups having 6 to 12 carbon atoms and in particular 2-ethylhexyl or 2-ethylheptyl.

Mixtures

In a further embodiment of the present invention, the dithiopyrrolopyrrole derivatives according to the invention may also be a constituent of mixtures.

Liquid-Crystalline Compounds.

The mixtures according to the invention comprise, in particular, liquid-crystalline compounds. They preferably comprise 3 to 25 different liquid-crystalline compounds, preferably 8 to 18, particularly preferably 12 to 16 different liquid-crystalline compounds. The liquid-crystalline compounds preferably represent the principal components of the mixture. They are particularly preferably present in the mixture, taken together, in a proportion of 90 to 99.99% by weight, particularly preferably 93 to 99.9% by weight and very particularly preferably 95 to 99.8% by weight.

The compounds of the formula (1) are preferably present in solution in the mixtures according to the invention. They are preferably influenced in their alignment by the alignment of the liquid-crystalline compounds.

The mixtures according to the invention are preferably liquid-crystalline materials. The mixtures are furthermore preferably thermotropic liquid-crystalline materials, but not lyotropic liquid-crystalline materials. The mixtures according to the invention preferably have a clearing point, particularly preferably a phase transition from a nematic liquid-crystalline state to an isotropic state, in the temperature range from 70° C. to 170° C., preferably from 90° C. to 160° C., particularly preferably from 95° C. to 150° C. and very particularly preferably from 105° C. to 140° C.

Furthermore, the dielectric anisotropy of the mixtures according to the invention is preferably greater than 3, particularly preferably greater than 7. However, the dielectric anisotropy of the mixtures according to the invention may also be negative. In this case, they preferably have a value of −0.5 to −10, particularly preferably of −1 to −8 and very particularly preferably of −2 to −6.

The mixtures according to the invention furthermore preferably have an optical anisotropy (Δn) of 0.01 to 0.3, particularly preferably of 0.04 to 0.27.

Liquid-crystalline compounds which can be used as constituents of the mixture according to the invention can be selected as desired in accordance with the general expert knowledge of the person skilled in the art.

The mixtures according to the invention preferably comprise, as liquid-crystalline compounds, one or more compounds which contain a nitrile group. It is furthermore preferred for the mixtures according to the invention to comprise, as liquid-crystalline compounds, at least one compound which contains structural elements based on 1,4-phenylenes and 1,4-cyclohexylenes. The mixtures according to the invention particularly preferably comprise, as liquid-crystalline compound, at least one compound which contains 2, 3 or 4, particularly preferably 3 or 4, structural elements based on 1,4-phenylenes and 1,4-cyclohexylenes.

Chiral Dopants.

The mixtures according to the invention furthermore preferably comprise one or more chiral dopants. Chiral dopants are preferably used in the mixtures according to the invention in a total concentration of 0.01 to 3% by weight, particularly preferably of 0.05 to 1% by weight. In order to obtain high values for the twist on use of the mixture in a device, the total concentration of the chiral dopants may also be selected higher than 3% by weight, preferably up to a maximum of 10% by weight.

According to an alternative, likewise preferred embodiment, the mixture according to the invention comprises no chiral dopants.

Stabilisers.

The mixtures according to the invention furthermore preferably comprise one or more stabilisers. The total concentration of the stabilisers is preferably between 0.00001 and 10% by weight, particularly preferably between 0.0001 and 1% by weight of the mixture.

Dye Compounds.

In addition to the at least one compound of the formula (1) and the at least one liquid-crystalline compound, the mixtures according to the invention preferably comprise one or more dye compounds having a different structure to formula (1). They particularly preferably comprise one, two, three or four dye compounds having a different structure to formula (1), very particularly preferably two or three dye compounds having a different structure to formula (1). These dye compounds are preferably dichroic dye compounds. They are furthermore preferably fluorescent dye compounds.

Regarding the property of dichroism, the preferred properties described for the compound of the formula (1) are also regarded as preferred for the optional further dye compounds having a different structure to formula (1).

The absorption spectra of the dye compounds of the mixtures according to the invention preferably complement one another in such a way that the impression of a black colour arises for the eye. The dye compounds of the mixture according to the invention preferably cover a large part of the visible spectrum. The precise way in which a mixture of dye compounds which appears black or grey to the eye can be prepared is known to the person skilled in the art and is described, for example, in Manfred Richter, Einführung in die Farbmetrik [Introduction to Colorimetry], 2nd Edition, 1981, ISBN 3-11-008209-8, Verlag Walter de Gruyter & Co.

The setting of the colour location of a mixture of dye compounds is described in the context of colorimetry. To this end, the spectra of the individual dyes are calculated taking into account the Lambert-Beer law to give an overall spectrum and converted into the corresponding colour locations and brightness values in accordance with the rules of colorimetry under the associated illumination, for example illuminant D65 for daylight. The position of the white point is determined by the respective illuminant, for example D65, and listed in tables (for example the above reference). Different colour locations can be set by changing the proportions of the various dye compounds.

The proportion of all dye compounds in the mixtures according to the invention, including the at least one compound of the formula (1), is preferably in total 0.01 to 10% by weight, particularly preferably 0.1 to 7% by weight and very particularly preferably 0.2 to 5% by weight.

The dye compounds having a different structure to formula (1) are preferably selected from the dye classes indicated in B. Bahadur, Liquid Crystals—Applications and Uses, Vol. 3, 1992, World Scientific Publishing, Section 11.2.1, and particularly preferably from the explicit compounds listed in the table present therein.

The dye compounds having a different structure to formula (I) are preferably selected from azo compounds, anthraquinones, methine compounds, azomethine compounds, merocyanine compounds, naphthoquinones, tetrazines, perylenes, terrylenes, quaterrylenes, higher rylenes, benzothiadiazoles and pyrromethenes. Of these, particular preference is given to perylenes, terrylenes, benzothiadiazoles and azo dyes.

The said dyes belong to the classes of dichroic dyes known to the person skilled in the art, which have been described many times in the literature. Thus, for example, anthraquinone dyes are described in EP 34832, EP 44893, EP 48583, EP 54217, EP 56492, EP 59036, GB 2065158, GB 2065695, GB 2081736, GB 2082196, GB 2094822, GB 2094825, JP-A 55-123673, DE 3017877, DE 3040102, DE 3115147, DE 3115762, DE 3150803 and DE 3201120, naphthoquinone dyes are described in DE 3126108 and DE 3202761, azo dyes are described in EP 43904, DE 3123519, WO 82/2054, GB 2079770, JP-A 56-57850, JP-A 56-104984, U.S. Pat. Nos. 4,308,161, 4,308,162, 4,340,973, T. Uchida, C. Shishido, H. Seki and M. Wada: mol. Cryst. Liq. Cryst. 39, 39-52 (1977) and H. Seki, C. Shishido, S. Yasui and T. Uchida: Jpn. J. Appl. Phys. 21, 191-192 (1982), and rylenes are described in EP 2166040, US 2011/0042651, EP 68427, EP 47027, EP 60895, DE 3110960 and EP 698649.

Susceptibility of Industrial Application

The present invention furthermore relates to the susceptibility of industrial application of the dyes according to the invention, as described below:

Regulation of the Entry of Light

In a first embodiment, the invention encompasses the use of the dithiopyrrolopyrrole derivatives of the formula (1) in a device for regulating the entry of light into a room.

A second embodiment is directed in the same mental association to a device which comprises the dithiopyrrolopyrrole derivatives of the formula (1) for regulating the entry of light into a room.

The device according to the invention is preferably suitable for regulating the entry of light in the form of light emitted by the sun from the environment into a room. The light entry to be regulated takes place here from the environment (the outside space) into a room. The room here can be any desired room which is substantially sealed off from the environment, for example a building, a vehicle or a container. The device can generally be used for any desired rooms, particularly if they have only limited exchange of air with the environment and have light-transmitting delimiting areas through which the input of energy from the outside in the form of light energy can take place. The use of the device is particularly relevant for rooms which are exposed to strong insolation through light-transmitting areas, for example through window areas.

In an alternative use, the device is employed for regulating the incidence of light on the eyes, for example in protective goggles, visors or sunglasses, where the device keeps the incidence of light on the eyes low in one switching state and reduces the incidence of light to a lesser extent in another switching state.

The device according to the invention is preferably arranged in an opening of a relatively large two-dimensional structure, where the two-dimensional structure itself does not allow the entry of light or only does so to a slight extent, and where the opening transmits light to a greater extent in relative terms. The two-dimensional structure is preferably a wall or another delimitation of a room from the outside. Furthermore preferably, the two-dimensional structure covers an at least equally large area, particularly preferably an at least twice as large area as the opening in it in which the device according to the invention is arranged.

The device according to the invention is preferably characterised in that it has an area of at least 0.05 $m^2$, preferably at least 0.1 $m^2$, particularly preferably at least 0.5 $m^2$ and very particularly preferably at least 0.8 $m^2$.

The device according to the invention is switchable. Switching here is taken to mean a change in the passage of light through the device. The device according to the invention is preferably electrically switchable.

If the device is electrically switchable, it preferably comprises two or more electrodes, which are installed on both sides of the switching layer comprising the mixture according to the invention. The electrodes preferably consist of ITO or a thin, preferably transparent metal and/or metal-oxide layer, for example silver or FTO (fluorine-doped tin oxide) or an alternative material known to the person skilled in the art for this use. The electrodes are preferably provided with electrical connections. The voltage is preferably provided by a battery, a rechargeable battery or an external power supply.

In the case of electrical switching, the switching operation takes place through alignment of the molecules of the mixture according to the invention by the application of voltage. In a preferred embodiment, the device is converted from a state having high absorption, i.e. low light transmissivity, which is present without voltage, into a state having lower absorption, i.e. higher light transmissivity, by application of a voltage. The mixture according to the invention in the layer in the device is preferably nematic in both states. The voltage-free state is preferably characterised in that the molecules of the mixture, and thus the molecules of the compound of the formula (1), are aligned parallel to the plane of the switching layer. This is preferably achieved by a correspondingly selected alignment layer. The state under voltage is preferably characterised in that the molecules of the mixture, and thus the molecules of the compound of the formula (1), are perpendicular to the plane of the switching layer.

In an alternative embodiment to the embodiment mentioned above, the device is converted from a state having low absorption, i.e. high light transmissivity, which is present without voltage, into a state having higher absorption, i.e. lower light transmissivity, by application of a voltage. The mixture according to the invention in the layer in the device is preferably nematic in both states. The voltage-free state is preferably characterised in that the molecules of the mixture, and thus the molecules of the compound of the formula (1), are aligned perpendicular to the plane of the switching layer. This is preferably achieved by a correspondingly selected alignment layer. The state under voltage is preferably characterised in that the molecules of the mixture, and thus the molecules of the compound of the formula (1), are parallel to the plane of the switching layer.

According to a preferred embodiment of the invention, the device can be operated without an external power supply by providing the energy required by means of a solar cell or another device for conversion of light and/or heat energy into electrical energy which is connected to the device. The provision of the energy by means of the solar cell can take place directly or indirectly, i.e. via a battery or rechargeable battery or other unit for the storage of energy connected in-between. The solar cell is preferably mounted on the outside of the device or is an internal component of the device, as disclosed, for example, in WO 2009/141295 A1. Preference is given here, in particular, to solar cells which are particularly efficient in the case of diffuse light, and transparent solar cells.

A device of this type may be distinguished by having the following layer sequence, where further layers may additionally be present:
- substrate layer;
- electrically conductive transparent layer;
- alignment layer;
- switching layer comprising the dithiopyrrolopyrrole derivatives;
- alignment layer;
- electrically conductive transparent layer;
- substrate layer.

The preferred embodiments of the individual layers are described below.

The device according to the invention preferably comprises one or more, particularly preferably two, alignment layers. The alignment layers are preferably directly adjacent to both sides of the layer comprising the mixture according to the invention.

The alignment layers used in the device according to the invention can be any desired layers known to the person skilled in the art for this purpose. Preference is given to polyimide layers, particularly preferably layers comprising rubbed polyimide. Polyimide rubbed in a certain manner known to the person skilled in the art results in alignment of the molecules of the liquid-crystalline medium in the rubbing direction if the molecules are parallel to the alignment layer (planar alignment). It is preferred here for the molecules of the liquid-crystalline medium not to be completely planar on the alignment layer, but instead to have a slight pretilt angle. In order to achieve vertical alignment of the compounds of the liquid-crystalline medium to the surface of the alignment layer (homeotropic alignment), polyimide treated in a certain manner is preferably employed as material for the alignment layer (polyimide for very high pretilt angles). Furthermore, polymers obtained by an exposure process to polarised light can be used as alignment layer in order to achieve alignment of the compounds of the liquid-crystalline medium in accordance with an alignment axis (photoalignment).

In the device according to the invention, the layer comprising the mixture according to the invention is furthermore preferably arranged between two substrate layers or enclosed thereby. The substrate layers can consist, for example, of glass or a polymer, preferably a light-transmitting polymer.

The device is preferably characterised in that it does not comprise a polymer-based polariser, particularly preferably does not comprise a polariser in the solid material phase and very particularly preferably comprises no polariser at all.

However, in accordance with an alternative embodiment, the device may also comprise one or more polarisers. The polarisers in this case are preferably linear polarisers.

If precisely one polariser is present, its absorption direction is preferably perpendicular to the orientation axis of the compounds of the liquid-crystalline medium of the device according to the invention on the side of the switching layer on which the polariser is located.

In the device according to the invention, both absorptive and also reflective polarisers can be employed. Preference is given to the use of polarisers which are in the form of thin optical films. Examples of reflective polarisers which can be used in the device according to the invention are DRPF (diffusive reflective polariser film, 3M), DBEF (dual brightness enhanced film, 3M), DBR (layered-polymer distributed Bragg reflectors, as described in U.S. Pat. Nos. 7,038,745 and 6,099,758) and APF films (advanced polariser film, 3M, cf. Technical Digest SID 2006, 45.1, US 2011/0043732 and U.S. Pat. No. 7,023,602). It is furthermore possible to employ polarisers based on wire grids (WGPs, wire-grid polarisers) which reflect infrared light. Examples of absorptive polarisers which can be employed in the devices according to the invention are the Itos XP38 polariser film and the Nitto Denko GU-1220DUN polariser film. An example of a circular polariser which can be used in accordance with the invention is the APNCP37-035-STD polariser (American Polarizers). A further example is the CP42 polariser (ITOS).

The device according to the invention furthermore preferably comprises an optical waveguide system which transports the light to a solar cell or another device for the conversion of light and/or heat energy into electrical energy, preferably as described in WO 2009/141295. The optical waveguide system collects and concentrates light hitting the device. It preferably collects and concentrates light emitted by fluorescent dichroic dyes in the switching layer. The optical waveguide system is in contact with a device for the conversion of light energy into electrical energy, preferably a solar cell, so that the collected light hits the latter in concentrated form. In a preferred embodiment of the invention, the device for the conversion of light energy into electrical energy is mounted at the edge of the device, integrated into the latter and electrically connected to means for the electrical switching of the device according to the invention.

In a preferred embodiment, the device according to the invention is a constituent of a window, particularly preferably a window comprising at least one glass surface, very particularly preferably a window which comprises multipane insulating glass.

Window here is taken to mean, in particular, a structure in a building which comprises a frame and at least one glass pane surrounded by this frame. It preferably comprises a heat-insulating frame and two or more glass panes (multipane insulating glass).

According to a preferred embodiment, the device according to the invention is applied directly to a glass surface of a window, particularly preferably in the interspace between two glass panes of multipane insulating glass.

Finally, in the same mental connection, a window containing or having a device as explained above is claimed.

Further Areas of Application

The present invention furthermore relates to the use of dithiopyrrolopyrrole derivatives of the formula (1)
(i) as semiconductor or sensitiser in electronic components, where these are preferably selected from the group formed by solar cells, diodes and transistors. Specific mention may be made here of LEDs, OLEDs, LETs and OLETs, and
(ii) for the colouring of polymers, for example polymer films, which can be employed, in particular, in vehicle manufacture,
(iii) in "guest-host" LCD applications.

For the present invention and in the following examples, the structures of the liquid-crystal compounds are indicated by acronyms, where the transformation into chemical formulae takes place in accordance with Tables A to C below. All radicals $C_nH_{2n+1}$, $C_mH_{2m+1}$ and $C_lH_{2l+1}$ or $C_mH_{2m}$ $C_mH_{2m}$ and $C_lH_{2l}$ are straight-chain alkyl radicals or alkylene radicals respectively, having n, m or 1C atoms respectively. The ring elements of the nuclei of the compounds are coded in Table A, the bridging elements are listed in Table B, and the meanings of the symbols for the left-hand or right-hand end groups of the molecules are listed in Table C. The acronyms are composed of the codes for the ring elements with optional linking groups, followed by a first hyphen and the codes for the left-hand end group, and a second hyphen and the codes for the right-hand end group.

TABLE A

Ring elements

| | | | |
|---|---|---|---|
| C | (trans-cyclohexane-1,4-diyl) | | |
| D | (1,3-dioxane-2,5-diyl) | DI | (1,3-dioxane-5,2-diyl) |
| A | (tetrahydropyran-2,5-diyl) | AI | (tetrahydropyran-5,2-diyl) |
| P | (1,4-phenylene) | | |
| G | (2-fluoro-1,4-phenylene) | GI | (3-fluoro-1,4-phenylene) |
| U | (2,3-difluoro-1,4-phenylene) | UI | (3,5-difluoro-1,4-phenylene) |
| Y | (2,3-difluoro-1,4-phenylene, alt.) | | |
| P(F,Cl) | (2-fluoro-3-chloro-1,4-phenylene) | P(Cl,F) | (2-chloro-3-fluoro-1,4-phenylene) |
| N | (pyridine-2,5-diyl) | NI | (pyridine-5,2-diyl) |
| M | (pyrimidine-2,5-diyl) | MI | (pyrimidine-5,2-diyl) |
| np | (naphthalene-2,6-diyl) | | |
| n3f | (trifluoronaphthalene-2,6-diyl) | n3fI | (trifluoronaphthalene-6,2-diyl) |

TABLE A-continued

Ring elements

| Code | Structure | Code | Structure |
|---|---|---|---|
| th | 2,6-tetrahydronaphthalene (tetralin) ring | thI | 6,2-tetrahydronaphthalene (tetralin) ring |
| tH2f | difluoro-tetrahydronaphthalene | tH2fI | difluoro-tetrahydronaphthalene (reversed) |
| o2f | difluoro-chroman | o2fI | difluoro-chroman (reversed) |
| dh | decahydronaphthalene | | |
| K | trifluoro-indane | KI | trifluoro-indane (reversed) |
| L | cyclohexene (1,4) | LI | cyclohexene (reversed) |
| F | fluorocyclohexene | FI | fluorocyclohexene (reversed) |

TABLE B

| | Bridging elements | | |
|---|---|---|---|
| E | —CH$_2$—CH$_2$— | Z | —CO—O— |
| V | —CH═CH— | ZI | —O—CO— |
| T | —C≡C— | X | —CF═CH— |
| W | —CF$_2$—CF$_2$— | XI | —CH═CF— |
| B | —CF═CF— | O | —CH$_2$—O— |
| | | OI | —O—CH$_2$— |
| | | Q | —CF$_2$—O— |
| | | QI | —O—CF$_2$— |

TABLE C

End groups

| On the left, standing alone or in combination | | On the right, standing alone or in combination | |
|---|---|---|---|
| -n- | C$_n$H$_{2n+1}$— | -n | —C$_n$H$_{2n+1}$ |
| -nO- | C$_n$H$_{2n+1}$—O— | -nO | —O—C$_n$H$_{2n+1}$ |
| -V- | CH$_2$═CH— | -V | —CH═CH$_2$ |
| -nV- | C$_n$H$_{2n+1}$—CH═CH— | -nV | —C$_n$H$_{2n}$—CH═CH$_2$ |
| -Vn- | CH$_2$═CH—C$_n$H$_{2n}$— | -Vn | —CH$_2$═CH—C$_n$H$_{2n+1}$ |
| -nVm- | C$_n$H$_{2n+1}$—CH═CH—C$_m$H$_{2m}$— | -nVm | —C$_n$H$_{2n}$—CH═CH—C$_m$H$_{2m+1}$ |
| -N- | N≡C— | -N | —C≡N |

TABLE C-continued

| End groups | | | |
|---|---|---|---|
| -S- | S=C=N— | -S | —N=C=S |
| -F- | F— | -F | —F |
| -CL- | Cl— | -CL | —Cl |
| -M- | CFH$_2$— | -M | —CFH$_2$ |
| -D- | CF$_2$H— | -D | —CF$_2$H |
| -T- | CF$_3$— | -T | —CF$_3$ |
| -MO- | CFH$_2$O— | -OM | —OCFH$_2$ |
| -DO- | CF$_2$HO— | -OD | —OCF$_2$H |
| -TO- | CF$_3$O— | -OT | —OCF$_3$ |
| -A- | H—C≡C— | -A | —C≡C—H |
| -nA- | C$_n$H$_{2n+1}$—C≡CH— | -An | —C≡C—C$_n$H$_{2n+1}$ |
| -NA- | N≡C—C≡C— | -AN | —C≡C—C≡N |

| On the left only in combination | | On the right only in combination | |
|---|---|---|---|
| - . . . n . . . - | —C$_n$H$_{2n}$— | - . . . n . . . | —C$_n$H$_{2n}$— |
| - . . . M . . . - | —CFH— | - . . . M . . . | —CFH— |
| - . . . D . . . - | —CF$_2$— | - . . . D . . . | —CF$_2$— |
| - . . . V . . . - | —CH=CH— | - . . . V . . . | —CH=CH— |
| - . . . Z . . . - | —CO—O— | - . . . Z . . . | —CO—O— |
| - . . . ZI . . . - | —O—CO— | - . . . ZI . . . | —O—CO— |
| - . . . K . . . - | —CO— | - . . . K . . . | —CO— |
| - . . . W . . . - | —CF=CF— | - . . . W . . . | —CF=CF— | in which n and m are each integers and the three dots " . . . " are place holders for other abbreviations from this table.

EXAMPLES

Preparation Example H1

Preparation of 3,6-di(thiophen-2-yl)pyrrolo[3,4-c]pyrrole-1,4(2H,5H)-dione (DKPP) (2)

Precursor (2) is prepared in accordance with the following reaction scheme (I):

(I)
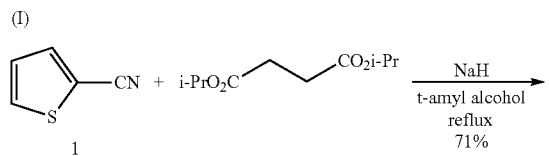

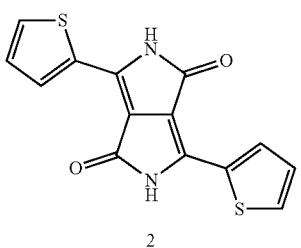

24.5 g (0.610 mol) of a 60% sodium hydride suspension are added in about 10 portions under nitrogen to 670 g of 2-methyl-2-butanol, and the foam which forms in the process is allowed to collapse. The cloudy solution is subsequently warmed to 60° C., during which a yellow solution forms, to which 66.7 g (0.610 mol) of 2-thiophenecarbonitrile (1) are added in one portion, giving a brownish dispersion. The temperature is increased to 100° C., during which the suspension clarifies, giving a brown solution. 49.4 g (0.244 mol) of diisopropyl succinate are added dropwise to the solution over a period of one hour, during which the solution is carefully heated to reflux. The resultant violet solution is then kept under reflux for a further 14 hours and then cooled to room temperature. The reaction batch is subsequently stirred slowly into 3 l of methanol, and 160 ml of glacial acetic acid are added, the mixture is stirred for a further 2 hours, and the precipitated solid is filtered off. The filter cake is washed with 3 l of water until the filtrate is colourless and rinsed once again with 1 l of O.P. IMS. The filter cake is subsequently dried overnight at 80° C. in a high vacuum, giving 52 g of DKPP (2), corresponding to a yield of 71% of theory.

HPLC evaluation: 99.8% (280 nm), 99.7% (530 nm);

Elemental analysis (C$_{14}$H$_8$N$_2$O$_2$S$_2$): theoretical C: 55.99%; H: 2.68%; N: 9.33%—found C: 55.73%; H: 2.61%; N: 9.17%.

The product can be classified as analytically pure.

Preparation Example H2

Preparation of 3,6-di(thiophen-2-yl)pyrrolo[3,4-c]pyrrole-1,4(2H,5H)-dithione (DTPP) (3)

Precursor (3) is prepared in accordance with the following reaction scheme (II):

(II)
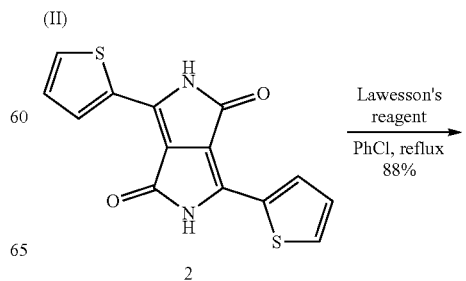

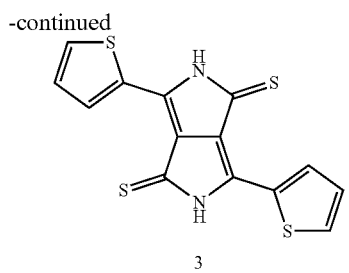

3

51.0 g (0.17 mol) of precursor (2) from Preparation Example H1 and 137 g (0.34 mol) of Lawes son's reagent are introduced into a 3 l flask under nitrogen, and 2 l of chlorobenzene are added. The mixture is heated under reflux under inert gas for 12 hours, during which the suspended solid changes colour from red via purple to black. The mixture is cooled to room temperature, filtered, and the filter cake is washed with 500 ml of methanol. The residue is subsequently resuspended in 2 l of methanol and stirred at 45 to 50° C. for one hour and filtered in the hot state. The filter cake is washed firstly with 1 l of methanol and then with 1 l of acetone and dried overnight in a desiccator, giving 55.0 g of DTPP (3) in the form of a black powder, which corresponds to a yield of 97% of theory.

HPLC evaluation: 94.8% (330 nm); 97.5% (625 nm)

Elemental analysis ($C_{14}H_8N_2O_2S_4$): theoretical N: 8.43%—found N: 7.57%.

Preparation Example H3

Preparation of 3,6-di(thiophen-2-yl)pyrrolo[3,4-c]pyrrole-[di-S-EtHex-DTTP] (4)

Precursor (4) is prepared in accordance with the following reaction scheme (III):

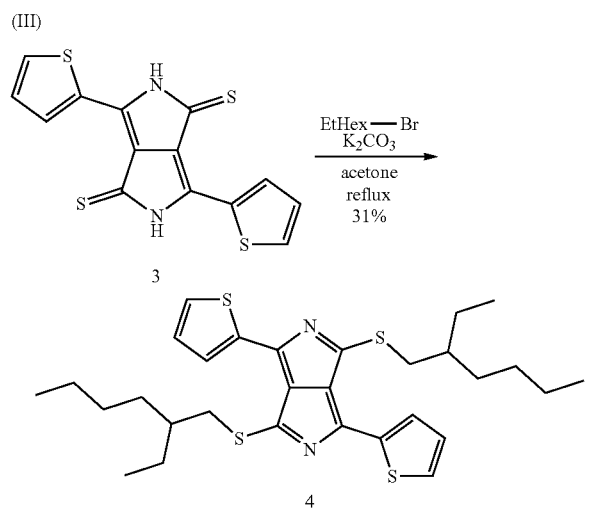

53.2 g (0.144 mol) of precursor (3) from Preparation Example H2, 88.3 g (0.64 mol) of potassium carbonate and 92.6 g (0.48 mol) of 2-ethylhexyl bromide are introduced into a 5 l flask under nitrogen, 3.2 l of acetone are added, and the mixture is kept under reflux for 24 h. After cooling to room temperature, inorganic salts are separated off, and the filtrate is evaporated to dryness, giving a black solid. This is dissolved in 200 ml of dichloromethane, and 1 l of heptane is added at elevated temperature. The dichloromethane is distilled off at 70° C. in a rotary evaporator. The solution which remains is transferred onto a silica gel bed (40-63μ, 1 kg, 19 cm Ø) which has been moistened with heptane. The bed is eluted with a 3:1 mixture of heptane and dichloromethane, giving 5×3 fractions; the operation is terminated when the eluate begins to discolour. The purest fractions 2 and 3 are combined and evaporated to dryness, giving 48.3 g of a black residue, corresponding to 54% of theory. The residue is resuspended in 100 ml of dichloromethane, and a further 500 ml of heptane are added at 40° C. The dichloromethane is subsequently separated off again at 70° C. in a rotary evaporator, and the remaining solution in 50 ml of hot heptane is filtered. The heptane is distilled off, leaving 500 ml of solution, which is left to stand overnight. The crystals which have precipitated out in this time are filtered off and washed on the filter firstly with two 30 ml portions of cold heptane (−20° C.) and then with two 30 ml portions of acetonitrile. Drying gives precursor (4) as black-violet crystals in an amount of 28.0 g, corresponding to 31% of theory.

HPLC evaluation: 99.3% (330 nm); 100% (550 nm); 98.5% (625 nm)

$^1$H-NMR: (CDCl$_3$, 500 MHz) δ 0.85 (6H, t, J 7.0), 0.92 (6H, t, J 7.5), 1.20-1.55 (16H, m), 1.76 (2H, m), 3.47 (4H, m), 7.20 (2H, m), 7.56 (2H, br. S), 8.03 (2H br. s).

Preparation Example H4

Preparation of 3,6-di(thiophen-2-yl)pyrrolo[3,4-c]pyrrole-[di-Br-di-S-EtHex-DTTP] (5)

Precursor (5) is prepared in accordance with the following reaction scheme (IV):

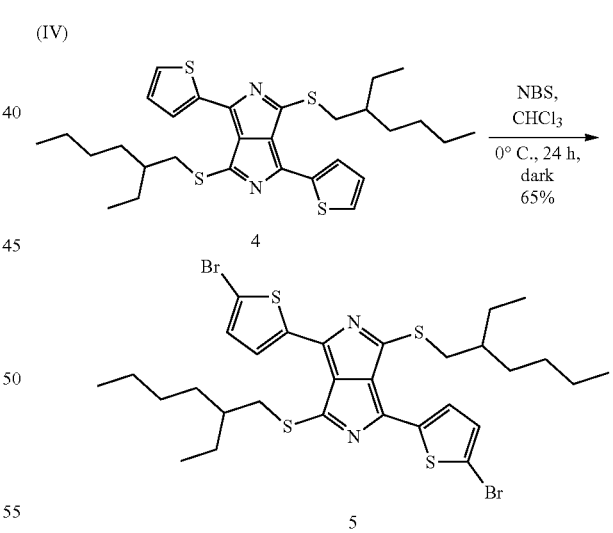

27.9 g (50 mmol) of precursor (4) from Preparation Example H3 are dissolved in 1.4 l of chloroform and cooled to −5° C. in an ice bath. The flask is covered with aluminium foil in order to exclude light, and a total of 19.1 g (107 mmol) of N-bromosuccinimide are then added in 10 portions over a period of one hour. The mixture is subsequently stirred at ambient temperature for 48 hours. It is subsequently concentrated to half its volume in vacuo, during which a solid deposits. This is re-dissolved by heating to 60° C., and 700 ml of methanol are then added, causing it to precipitate out again. The mixture is then again concentrated to half its volume, a further 700 ml of methanol are added, the mixture is rapidly warmed to 60° C. for 5 minutes and filtered while hot. The residue is washed on the filter with 4 300 ml portions of methanol until the originally brownish filtrate becomes colourless. Drying gives precursor (5) as a black powder in an amount of 23.4 g, corresponding to 65% of theory.

HPLC evaluation: 99.4% (330 nm); 100% (550 nm); 99.7% (625 nm)

$^1$H-NMR: (CDCl$_3$, 500 MHz) δ 0.94 (6H, t, J 7.0), 0.98 (6H, t, J 7.5, 1H, m), 3.45 (2H, dd, J 6.5, J 13.5), 3.54 (2H, dd, J 6.0, J 13.5), 7.22 (2H, d, J 4.0, 7.81, d, J 4.0).

PREPARATION EXAMPLE H5

Preparation of 1,4-bis-(5-(4-(3-ethylheptyl)-2-fluorophenyl)thiophen-2-yl)-3,6-bis((2-ethylhexyl)thio)pyrrolo[3,4-c]pyrrole (6)

Product (6) according to the invention is prepared in accordance with the following reaction scheme (V):

the mixture is kept under reflux under nitrogen over a period of 6 hours, before being cooled overnight. After filtration, the solution is transferred into a separating funnel, and the lower aqueous phase is separated off and discarded. The organic phase is dried using sodium sulfate and then evaporated to dryness, giving a green-black oily, semi-solid mass. This residue is taken up in a minimal amount of a 50:50 mixture of dichloromethane/heptane and passed through a silica column (40-63μ, 200 g, 5 cm Ø) packed with the same solvent. The column is eluted with the eluent, and 50 ml fractions are taken off until the eluate begins to change colour to green. The product-rich fractions 2 to 4 are combined and freed from solvent, giving 2.1 g of a black solid, corresponding to 79% of theory. The solid is recrystallised from 50 ml of 2-butanone, the residue is filtered off and washed with HPLC-pure acetone on the filter before being freed from residual solvent in a drying cabinet at 40° C., giving dye (6) according to the invention as bronze-coloured microcrystals in an amount of 1.56 g, corresponding to 59% of theory.

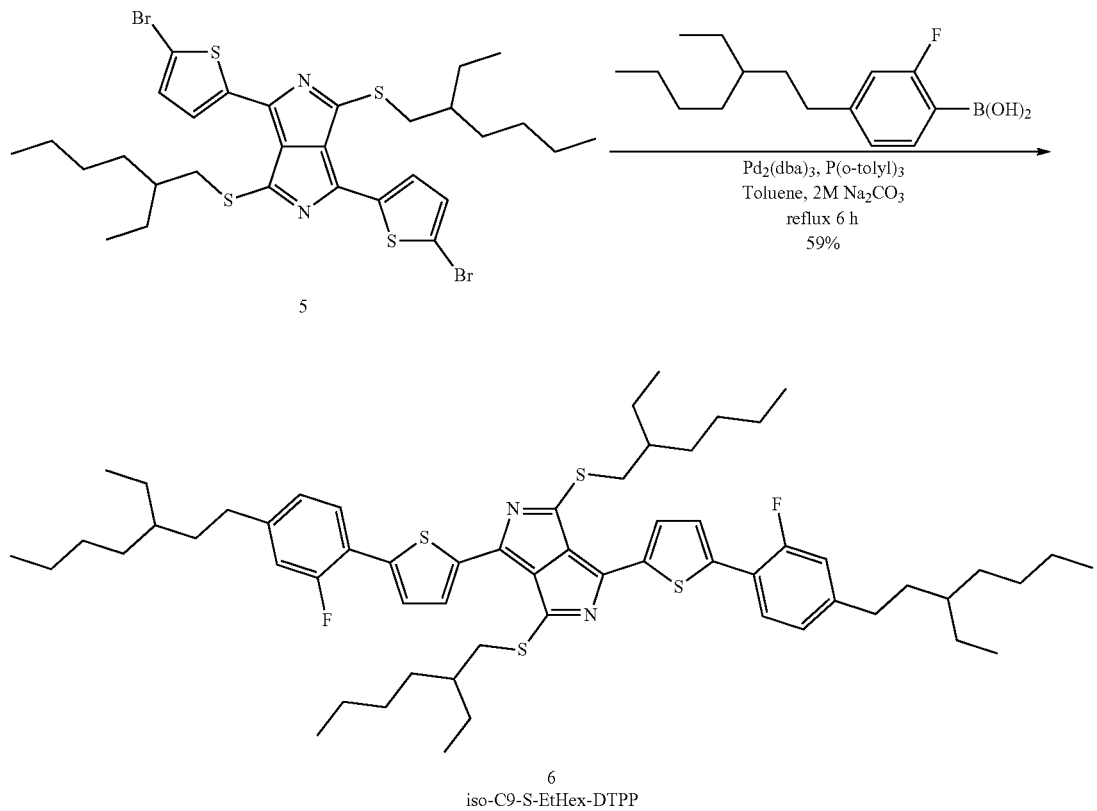

1.63 g (6.12 mmol) of (4-(3-ethylheptyl)-2-fluorophenyl) boric acid and 1.90 g (2.66 mmol) of precursor (5) from Preparation Example H4 are introduced into a flask, 70 ml of toluene and 12 ml of water are added, and the mixture is stirred vigorously. The mixture is degassed and placed under nitrogen three times, before 2.54 g (24.9 mmol) of sodium carbonate, 0.155 g (0.377 mmol) of tris(o-tolyl)phosphine and 0.086 g (0.094 mmol) of tris(dibenzylidene)dipalladium are added. The flask is provided with a reflux condenser, and HPLC evaluation: 99.0% (280 nm); 99.5% (370 nm); 99.4% (470 nm), 99.5% (600 nm), 99.4% (650 nm)

UV-VIS (CDCl$_3$) λ$_{max}$ 656 nm (61,000, FWHM 105 nm), 609 (46,500), 473 (30,000, FWHM 48 nm), 370 (28,500)

$^1$H-NMR: (CDCl$_3$, 500 MHz) δ 0.86-0.95 (18H, m), 1.01 (6H, t, J 7.5), 1.20-1.65 (38H, m), 1.85 (2H, m), 2.61 (4H, m), 3.51 (2H, dd, J 6.5 J 13.0), 3.60 (2H, dd, J 6.0, J 13.0), 6.97-7.05 (4H, m), 7.59-7.66 (4H, m), 8.10 (2H, d, J 4.0).

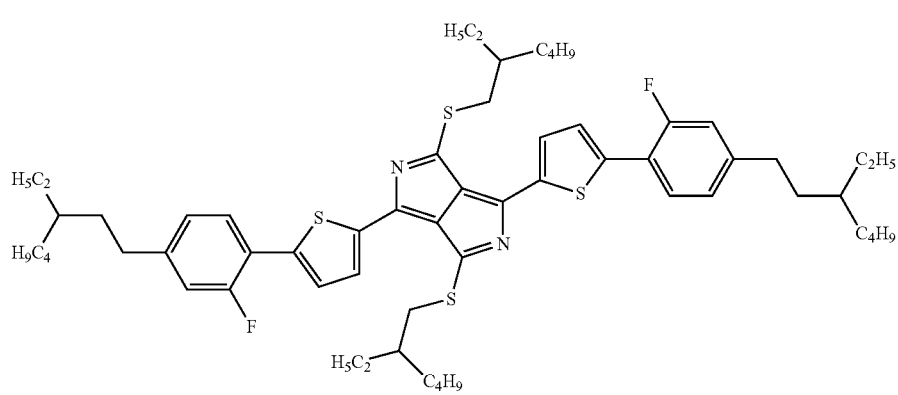

dye 1

Base Mixture
Above and below,
Δn denotes the optical anisotropy measured at 20° C. and 589 nm,
$n_e$ denotes the extraordinary refractive index measured at 20° C. and 589 nm,
$n_o$ denotes the ordinary refractive index measured at 20° C. and 589 nm,
Δε denotes the dielectric anisotropy at 20° C. and 1 kHz,
cl.p., T(N,I) denotes the clearing point [° C.].

| Phys. properties | Substance | Percent by weight % |
|---|---|---|
| cl.p.: 114.5° C. | CPG-3-F | 5 |
|  | CPG-5-F | 5 |
| Δn: 0.1349 | CPU-3-F | 15 |
| $n_e$: 1.6303 | CPU-5-F | 15 |
| $n_o$: 1.4954 | CP-3-N | 16 |
|  | CP-5-N | 16 |
| Δε: 11.3 | CCGU-3-F | 7 |
|  | CGPC-3-3 | 4 |
|  | CGPC-5-3 | 4 |
|  | CGPC-5-5 | 4 |
|  | CCZPC-3-3 | 3 |
|  | CCZPC-3-4 | 3 |
|  | CCZPC-3-5 | 3 |

Mixture Example 1

99.75% of base mixture+0.25% of dye 1
The dye exhibits a degree of anisotropy of 0.64 at 664 nm.
The extinction coefficients are:

| Wavelength | | 1/[% * cm] |
|---|---|---|
| 664 nm | ε_parallel | 1527 |
| 664 nm | ε_perpendicular | 238 |
| 479 nm | ε_parallel | 500 |
| 479 nm | ε_perpendicular | 254 |

Use Example 1

A mixture of the following composition is prepared:
99.15% of base mixture,
0.251% of dye 1
0.165% of dye 2
0.236% of dye 3
0.198% of dye 4

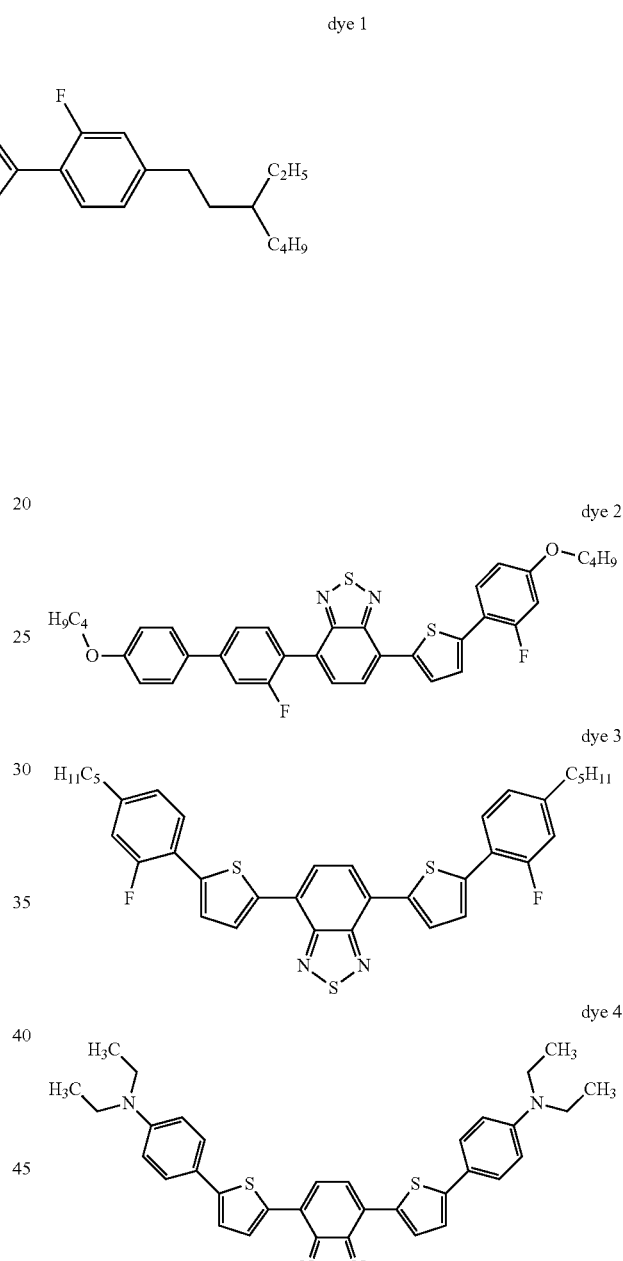

In a 90° twisted TN cell having a thickness of 25 microns, the mixture exhibits a degree of light transmission in accordance with EN410 in the dark state of 40% and a degree of light transmission in accordance with EN410 in the bright state of 71.5%.

The colour coordinates of the dark state are precisely neutral grey: x=0.3127 and y=0.3290 (CIE 1931) and standard illuminant D65.
The colour coordinates of the bright state are: x=0.3167 and y=0.3379 (CIE 1931) and standard illuminant D65.

Use Example 2

A mixture of the following composition is prepared:
99.588% of base mixture,
0.178% of dye 1

0.048% of dye 2
0.162% of dye 3
0.024% of dye 4

In a set-up comprising two 90° twisted TN cells having a thickness of 25 microns in series, the mixture exhibits a degree of light transmission in accordance with EN410 in the dark state of 30% and a degree of light transmission in accordance with EN410 in the bright state of 73%.

The colour coordinates of the dark state are precisely neutral grey: x=0.3127 and y=0.3290 (CIE 1931) and standard illuminant D65.

The colour coordinates of the bright state are: x=0.3207 and y=0.3472 (CIE 1931) and standard illuminant D65.

The invention claimed is:

1. A dithiopyrrolopyrrole compound of formula (1)

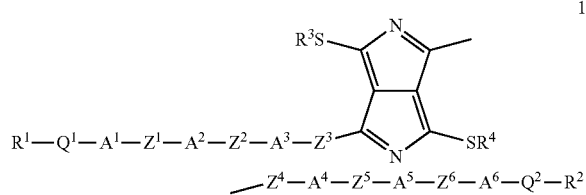

in which
R$^1$ and R$^2$ are each, independently of one another, a linear or branched, optionally halogen-substituted alkyl group having 1 to 20 carbon atoms;
R$^3$ and R$^4$ are each, independently of one another, a linear or branched, optionally halogen-substituted alkyl group having 1 to 20 carbon atoms or halogen;
Q$^1$ and Q$^2$ are each, independently of one another, a single bond O, OCF$_2$, CF$_2$, CF$_2$CF$_2$ or CO;
A$^1$, A$^2$, A$^3$, A$^4$, A$^5$ and A$^6$ are each, independently of one another, a single bond or an aromatic ring, each of which is selected from the group consisting of phenylene, pyridine, pyrimidine, pyridazine, naphthylene, thiophene, selenophene and thiazole,
with the provisos that
(i) at least A$^3$ and A$^4$ are aromatic rings, and
(ii) the aromatic rings are optionally substituted by halide; and
Z$^1$, Z$^2$, Z$^3$, Z$^4$, Z$^5$ and Z$^6$ are each, independently of one another, a single bond, C≡C, CH═CH, CF═CF, CF═CH, CH$_2$CH$_2$, CF$_2$—CF$_2$ or CF$_2$O,
with the proviso that
(iii) at least Z$^3$ and Z$^4$ represent either single bonds or a π-conjugated group.

2. The dithiopyrrolopyrrole compound according to claim 1, wherein R$^1$, R$^2$, R$^3$ and R$^4$ are each, independently of one another, a branched alkyl having 6 to 12 carbon atoms.

3. The dithiopyrrolopyrrole compound according to claim 1, in which 3, 4 or 5 of A$^1$, A$^2$, A$^3$, A$^4$, A$^5$ and A$^6$ are aromatic rings.

4. The dithiopyrrolopyrrole compound according to claim 1, wherein the A$^1$, A$^2$, A$^3$, A$^4$, A$^5$ and A$^6$, which are aromatic rings, are substituted by fluoride.

5. The dithiopyrrolopyrrole compound according to claim 1, which has one or more mesophases at a temperature below about 200° C.

6. The dithiopyrrolopyrrole compound according to claim 1, wherein Q$^1$ and Q$^2$ are single bonds.

7. The dithiopyrrolopyrrole compound according to claim 1, wherein Q$^1$ and Q$^2$ are independently of one another, O, OCF$_2$, CF$_2$, CF$_2$CF$_2$ or CO.

8. The dithiopyrrolopyrrole compound according to claim 1, wherein R$^1$ and R$^2$ are each, independently of one another, a linear or branched, alkyl group having 1 to 20 carbon atoms.

9. A method for regulating the entry of light into a room comprising letting said light into the room through a device, which comprises the dithiopyrrolopyrrole compound according to claim 1.

10. A device for regulating the entry of light into a room, comprising the dithiopyrrolopyrrole compound of formula (1) according to claim 1.

11. The device according to claim 10, which has the following layer sequence, where further layers may additionally be present:
substrate layer;
electrically conductive transparent layer;
alignment layer;
switching layer comprising the dithiopyrrolopyrrole compound of formula (1);
alignment layer;
electrically conductive transparent layer;
substrate layer.

12. A window containing the device according to claim 10.

13. A semiconductor or sensitiser in an electronic component containing at least one dithiopyrrolopyrrole compound of formula (1) according to claim 1.

14. A solar cell, diode or transistor containing at least one dithiopyrrolopyrrole compound of formula (1) according to claim 1.

15. A method for the colouring of a polymer comprising adding to said polymer at least one dithiopyrrolopyrrole compound of formula (1) according to claim 1.

16. A guest-host application containing at least one dithiopyrrolopyrrole compound of formula (1) according to claim 1.

17. A dithiopyrrolopyrrole compound of formula 2, 3, 4, 5 or 6

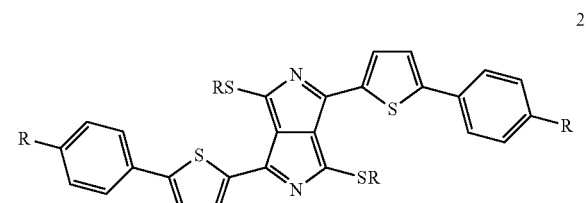

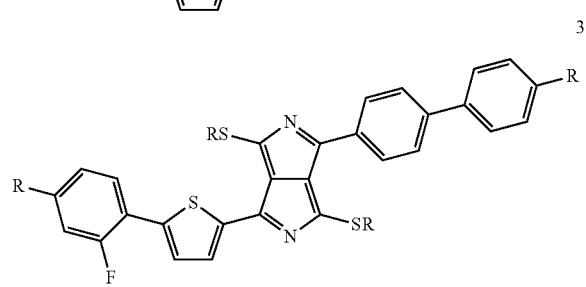

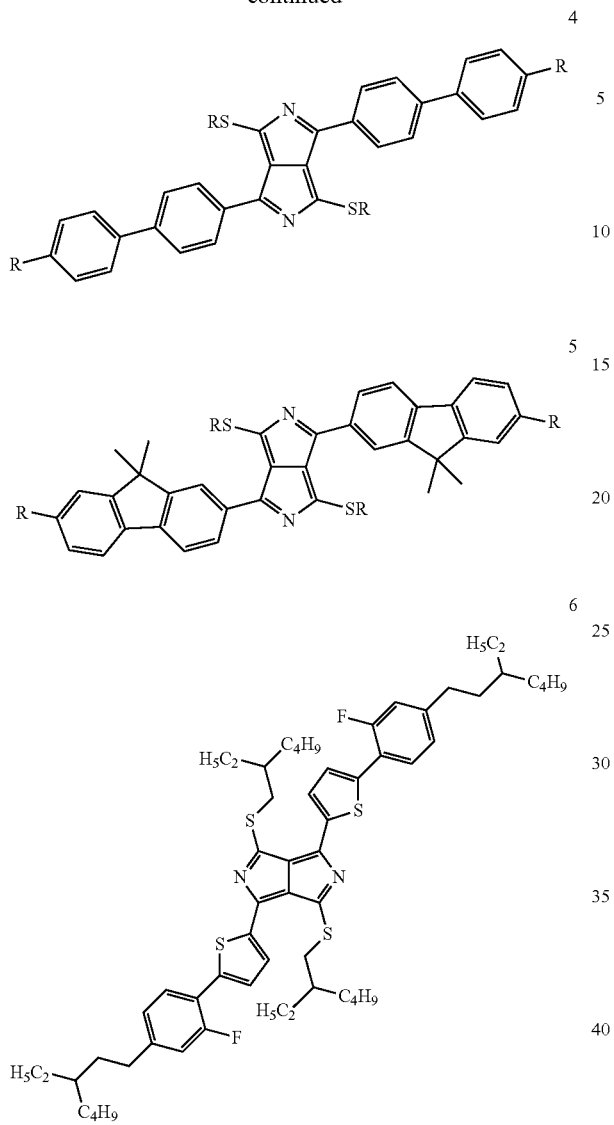

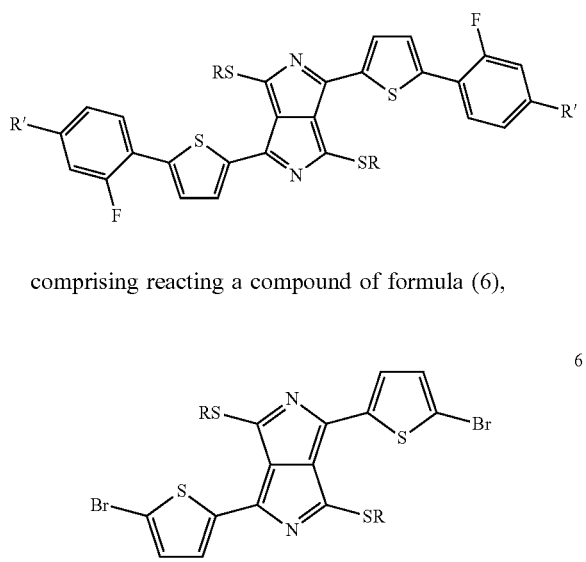

comprising reacting a compound of formula (6),

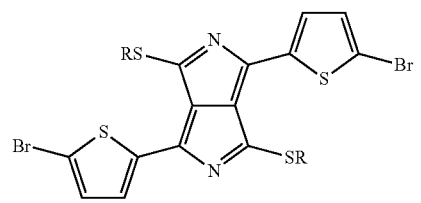

with a compound (6a),

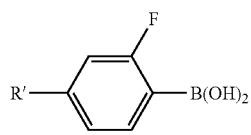

in which

R and R' are each, independently of one another, a linear or branched, optionally halogen-substituted alkyl group having 1 to 20 carbon atoms or halogen, in the presence of a catalytic amount of a homogeneous transition-metal complex.

20. A mixture comprising
(a) at least one dithiopyrrolopyrrole compound of formula (1)

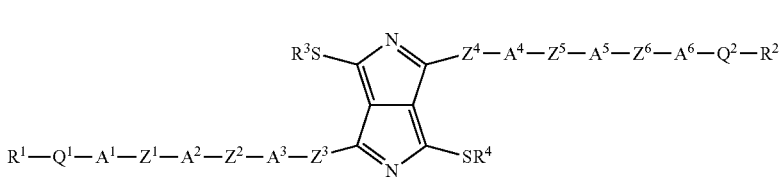

in which

R are each, independently of one another, a linear or branched, optionally halogen-substituted alkyl group having 1 to 20 carbon atoms or halogen.

18. A semiconductor or sensitiser in an electronic component, comprising at least one dithiopyrrolopyrrole compound according to claim 17.

19. A process for the preparation of a dithiopyrrolopyrrole compound of formula (7), in which $R^1$ and $R^2$ are each, independently of one another, a linear or branched, optionally halogen-substituted alkyl group having 1 to 20 carbon atoms;

$R^3$ and $R^4$ are each, independently of one another, a linear or branched, optionally halogen-substituted alkyl group having 1 to 20 carbon atoms or halogen;

$Q^1$ and $Q^2$ are each, independently of one another, a single bond O, $OCF_2$, $CF_2$, $CF_2CF_2$ or CO;

$A^1$, $A^2$, $A^3$, $A^4$, $A^5$ and $A^6$ are each, independently of one another, a single bond or an aromatic ring, each of which is selected from the group consisting of phenylene, pyridine, pyrimidine, pyridazine, naphthylene, thiophene, selenophene and thiazole, with the provisos that (i) at least $A^3$ and $A^4$ are aromatic rings, and (ii) the aromatic rings are optionally substituted by halide; and $Z^1$, $Z^2$, $Z^3$, $Z^4$, $Z^5$ and $Z^6$ are each, independently of one another, a single bond, C≡C, CH=CH, CF=CF, CF=CH, $CH_2CH_2$, $CF_2$—$CF_2$ or $CF_2O$, with the proviso that (iii) at least $Z^3$ and $Z^4$ represent either single bonds or a π-conjugated group, and (b1) at least one liquid-crystalline compound and/or (b2) at least one chiral dopant and/or (b3) at least one stabiliser and/or (b4) at least one dichroic dye.

21. The mixture according to claim 20, comprising (a) said at least one dithiopyrrolopyrrole compound of formula (1), and (b1) at least one liquid-crystalline compound and (b2) at least one chiral dopant and/or (b3) at least one stabiliser and/or (b4) at least one dichroic dye.

22. A window containing a device for regulating the entry of light into a room, comprising at least one dithiopyrrolopyrrole compound of formula 2, 3, 4, 5 or 6

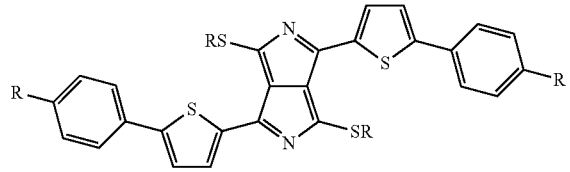

2

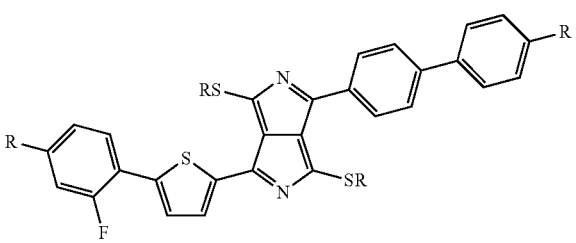

3

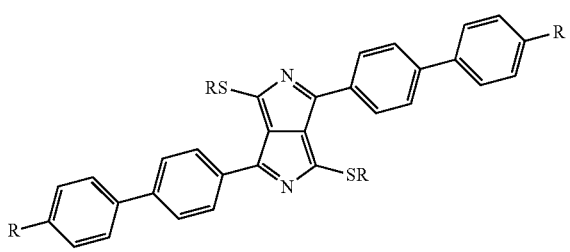

4

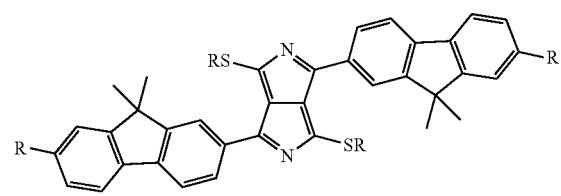

5

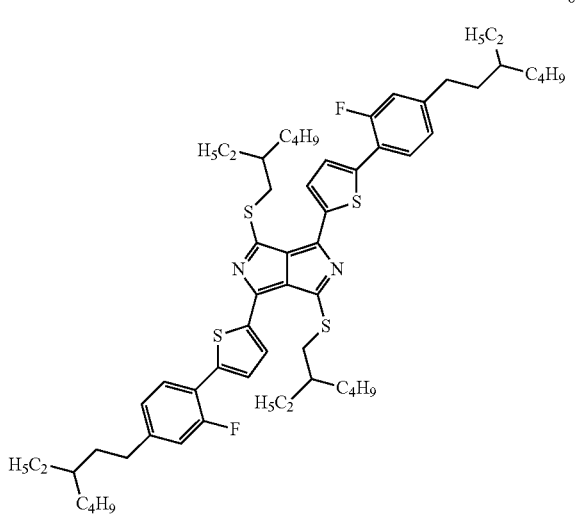

6 in which

R are each, independently of one another, a linear or branched, optionally halogen-substituted alkyl group having 1 to 20 carbon atoms or halogen.

23. The window containing a device for regulating the entry of light into a room according to claim 22, wherein, in the at least one dithiopyrrolopyrrole compound of formula 2, 3, 4 or 5, R are each, independently of one another, a branched alkyl having 6 to 12 carbon atoms.

* * * * *